US006518247B1

(12) United States Patent
Petukhov et al.

(10) Patent No.: US 6,518,247 B1
(45) Date of Patent: Feb. 11, 2003

(54) METHOD FOR PRODUCING AN ANTITUMORAL AGENT AND ANTITUMORAL AGENT THUS OBTAINED

(75) Inventors: Dmitriy Victorovich Petukhov, Saint-Petersbourg (RU); Valeriy Aphanasievich Trophimov, Saint-Petersbourg (RU); Vladimir Alexandrovich Philov, Saint-Petesbourg (RU); Valentina Vasilievna Reztsova, Saint-Petersbourg (RU); Boris Timopheievich Pinchuk, Saint-Petersbourg (RU)

(73) Assignee: Obschestvo s Ogranichennoi Otvetstvennostiju "Ligpharm", Moscow (RU)

( * ) Notice: Subject to any disclaimer, the term of this patent is extended or adjusted under 35 U.S.C. 154(b) by 0 days.

(21) Appl. No.: 09/831,833

(22) PCT Filed: Dec. 29, 1999

(86) PCT No.: PCT/RU99/00511

§ 371 (c)(1),
(2), (4) Date: May 15, 2001

(87) PCT Pub. No.: WO00/40257

PCT Pub. Date: Jul. 13, 2000

(30) Foreign Application Priority Data

Dec. 30, 1998 (RU) ............................................ 98123959

(51) Int. Cl.$^7$ ...................... A61K 35/78; A61K 33/14; A61K 33/42
(52) U.S. Cl. .................... 514/22; 424/601; 424/603; 424/606; 424/666; 424/680; 424/725
(58) Field of Search ........................... 514/22; 424/725, 424/606, 603, 601, 666, 680

(56) References Cited

U.S. PATENT DOCUMENTS 5,554,596 A * 9/1996 Mack et al. ................. 514/22

FOREIGN PATENT DOCUMENTS

| GB | 2 229 919 A | * 10/1990 |
| RU | 2102083 | 1/1998 |

OTHER PUBLICATIONS

Remington's Pharmaceutical Sciences, 16th Ed., Osol et al, editors, pp. 242–243, 1980.*

* cited by examiner

*Primary Examiner*—Francisco Prats
(74) *Attorney, Agent, or Firm*—Collard & Roe, P.C.

(57) ABSTRACT

In order to lower the painfulness of injection of the remedy containing the products of lignin basic hydrolysis and oxidation, pyrophosphate, NaCl and water the value of pH of the remedy is adjusted to a neutral one by the addition of HCl.

2 Claims, No Drawings

METHOD FOR PRODUCING AN ANTITUMORAL AGENT AND ANTITUMORAL AGENT THUS OBTAINED

CROSS REFERENCE TO RELATED APPLICATIONS

Applicants claim priority under 35 U.S.C. §119 of Russian Application No. 98123959 filed Dec. 30, 1998. Applicants also claim priority under 35 U.S.C. §120 of PCT/RU99/00511 filed Dec. 29, 1999. The international application under PCT article 21(2) was not published in English.

TECHNICAL FIELD OF THE INVENTION

The present invention relates to the process for producing antitumorous remedy and to the composition of the antitumorous remedy.

PRIOR ART

The method has been previously proposed for producing antitumorous remedy which comprises hydrolysis-extraction of the medicinal lignin in the basic medium in the field of ultrasonic oscillations, oxidizing the treated lignin with oxygen-containig gas, separating and acidifying the liquid phase, separating the obtained precipitate, washing the precipitate till neutral pH-value is reached, drying the precipitate, blending it with pyrophosphate, dissolving the blend in water while heating and adding NaCl with the obtainment of the desired product (RU, 2102083, C1, 20.01.98).

The antitumorous remedy has been previously proposed, which contains 200 mg of the product of lignin hydrolysis and oxidation, 2 ml of sodium pyrophosphate in the form of the 0.2 M solution and 8 ml of the physiological salt solution (RU, 2102083, C1, 20.01.98)

The drawback of said method and the remedy obtained according to it lies in that the injections of said remedy are painful.

DISCLOSURE OF THE INVENTION

The technical result of the invention is the decrease of the painfulness of the obtained remedy injections.

This result is achieved in the following way. In the method for producing the antitumorous remedy involving hydrolysis-extraction of lignin-containing raw material in the basic medium, oxidation of the treated material with oxygen-containing gas, separation of the liquid phase and its acidification, separation of the precipitate obtained and its washing till neutral pH-value is reached, drying the precipitate, blending it with pyrophosphate, dissolution of the blend in water while heating and addition of NaCl into the dissolved blend with the obtainment of the desired product, according to the invention HCl is added into the product till neutral pH-value is reached and the product of lignin basic hydrolysis and oxidation is mixed with pyrophosphate at a dry mass ratio of 25:17 accurate up to 10%.

The same result is achieved in that the antitumorous remedy containing the product of lignin basic hydrolysis and oxidation, pyrophosphate, NaCl and water, according to the invention additionally contains HCl and the components are used in the following proportion by mass to an accuracy of 10%:

| | |
|---|---|
| product of lignin hydrolysis and oxidation | 25 |
| pyrophosphate | 17 |
| NaCl | 3 |
| HCl | in the amount adjusting pH to 7.0 |
| water | up to 1000 |

BEST MODE FOR CARRYING OUT THE INVENTION

The method is carried out in the following way.

The lignin-containing raw material, for example the medicinal lignin or woods is subjected to the basic hydrolysis-extraction. When conducting this process in the field of ultrasonic oscillations its rate increases which results in raising the capacity. The products of hydrolysis are oxidized, for example with oxygen or air. Then the reaction mixture is cooled and acidified till the precipitate is formed. The precipitate is separated by one of the known methods, for example by filtration. The separated precipitate is washed by water or water-alcohol mixture till reaching a neutral pH-value and dried. After this the precipitate is blended with the salt of pyrophosphoric acid at a dry mass ratio of 25:17 accurate up to 10% in terms of pyrophosphate ion; the blend is dissolved in water while heating, for example in a water bath. NaCl is added to the blend in the amount of 3 mass parts accurate up to 10% in the form of the dry matter or the physiological salt solution and HCl is added to the blend till reaching a neutral pH-value within the same accuracy.

EXAMPLE

The prepared remedy contains 25 g of the dry powdered product of lignin hydrolysis and oxidation, 42 g of the crystalline hydrate of sodium pyrophosphate ($Na_4P_2O_7 \cdot 10H_2O$) according to ROCT 342-77, 3 g of NaCl, HCl in the amount adjusting pH to 7.0 and water up to 1000 ml The remedy is packed in the 1 ml ampoules and sterilized for utilization.

According to the experimental data the remedy thus obtained and the remedy produced according to the closest analogue are characterized by the same antitumorous activity studied on the different kinds of mise in relation to the solid Erlich's tumour, carcinosarcoma Ca 755, spontaneous mastoncus in mice and Woker's carcinosarcoma in rats. However, the effect of pain caused by the remedies injection and evaluated by the development of edema and also indirectly by the pulse and breathing frequency increase and normalization was significantly lower in case of the remedy obtained per the proposed method.

INDUSTRIAL USABILITY

The invention may be used in the production of the remedy for treating the oncological diseases.

What is claimed is:
1. A method for the production of an antitumorous remedy which comprises hydrolysis-extracting of lignin-containing raw material in a basic medium, oxidizing of treated material with oxygen-containing gas, separating of the liquid phase and its acidification, separating of a precipitate obtained and washing the precipitate until neutral pH-value is reached, drying the precipitate, blending the precipitate with pyrophosphate, dissolution of the blend in water while heating and adding NaCl into the dissolved blend thereby obtaining the desired product, adding HCl into the desired product until neutral pH-value is reached and the product of lignin basic hydrolysis and oxidation is mixed with pyrophosphate at a dry mass ratio of 25:17 accurate up to ±10%.

2. An antitumorous remedy containing the product of lignin basic hydrolysis and oxidation, pyrophosphate, NaCl and water, wherein it additionally contains HCl and the components are used in the following proportion by mass to an accuracy of ±10%:

| | |
|---|---|
| product of lignin hydrolysis and oxidation | 25 |
| pyrophosphate | 17 |
| NaCl | 3 |
| HCl | in the amount adjusting pH to 7.0 |
| water | up to 1000. |

* * * * *